United States Patent [19]

Micchia et al.

[11] Patent Number: 4,719,909
[45] Date of Patent: Jan. 19, 1988

[54] UNDER-EYE LIGHT ABSORBING DEVICE AND METHOD

[76] Inventors: Ronald L. Micchia; Sandra K. Micchia, both of 8558 Harvest Home Dr., Mentor, Ohio 44060

[21] Appl. No.: 917,968

[22] Filed: Oct. 14, 1986

Related U.S. Application Data

[63] Continuation-in-part of Ser. No. 852,107, Apr. 14, 1986, abandoned.

[51] Int. Cl.⁴ ............................................. A61L 15/00
[52] U.S. Cl. .................................................. 128/156
[58] Field of Search ............... 128/156; 132/88.5, 58.7

[56] References Cited

U.S. PATENT DOCUMENTS

| | | | |
|---|---|---|---|
| 1,532,238 | 4/1925 | Farrell | 132/88.5 |
| 1,850,540 | 3/1932 | Erickson | 132/88.5 |
| 2,234,657 | 3/1941 | Smaldore | 132/88.5 |
| 2,239,040 | 4/1941 | Holmes | 132/88.5 |
| 2,842,142 | 7/1958 | Peck | 132/88.5 |

Primary Examiner—Gregory E. McNeill

[57] ABSTRACT

An under-eye light absorbing device and method comprising utilizing a light absorbing replaceable sheet material patch attachable by pressure sensitive adhesive to the zygomatic arch skin area adjacent to the lower side of the user's orbit. The light absorbing surface may be black. The dispensing of the patch seriatim is facilitated by carrying the same on a ribbon in a roll which is housed in a dispenser box.

16 Claims, 4 Drawing Figures

UNDER-EYE LIGHT ABSORBING DEVICE AND METHOD

This invention is a continuation-in-part of our co-pending application Ser. No. 852,107 filed Apr. 14, 1986, now abandoned.

BACKGROUND OF THE INVENTION

This invention relates to a new and improved means and method for avoiding reflection into the eyes of incident light rays from the skin areas on the zygomatic arches along the lower side of the orbit, such areas being often referred to as the cheekbones.

Heretofore it has been common practice to coat the zygomatic arch skin areas with a light absorbing fluid film applied by some sort of dauber, such as a brush, fingertip or the like. Often such fluid materials have comprised substances which may be generally described as greasepaint. Such prior greasepaint type of antiglare materials have had numerous drawbacks among which may be mentioned having a tendency to contaminate headgear in athletic events, sweat-caused running, tending to be wiped off when wiping sweat from the face, and the need to scrub off to remove the greasy films, often necessitating special creams or detergents. Grease film can oftentimes enter the eye and contribute to and/or cause eye inflammation.

SUMMARY OF THE PRESENT INVENTION

An important object of the present invention is to provide new and improved under-eye light absorbing means and method which will overcome the disadvantages, drawbacks, inefficiencies, shortcomings and problems inherent with the prior expedience.

Another object of the invention is to provide a new and improved under-eye light absorbing device which can be easily applied and easily stripped in one piece as desired.

A further object of the invention is to provide a new and improvde under-eye light absorbing device and method involving simple, inexpensive, easily applied and removed patches.

To this end, the invention provides an under-eye light absorbing device comprising a replaceable pliable sheet material patch having a first side for generally conformable application to a skin area on the zygomatic arch along the lower side of the orbit of a user, adhesive means on the first face of the patch for strippable adhesive retention of the patch on the skin area, and a light absorbing surface on the other second face of the patch for absorbing incident light rays directed toward such skin area.

The present invention also provides a method of absorbing incident light from the zygomatic arch skin area along the lower side of the orbit, and comprising applying a light absorbing pliable sheet material patch to such skin area, and adhesively attaching the patch to such skin area.

BRIEF DESCRIPTION OF THE DRAWINGS

Other objects, features, and advantages of the present invention will be readily apparent from the following description of representative embodiments thereof, taken in conjunction with the accompanying drawings, although variations and modifications may be effected without departing from the spirit and the scope of the novel concepts embodied in the disclosure, and in which.

DETAILED DESCRIPTION OF THE PREFERRED EMBODIMENTS

Figure 1:
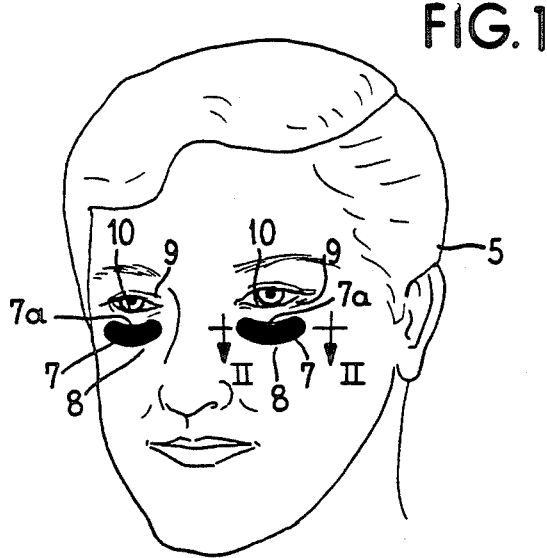
FIG. 1 is a schematic representation of a human head showing how the present invention is applied.

Referring to FIG. 1., there is shown a schematic human head 5 having under-eye light absorbing patches 7 embodying the present invention applied to the skin areas over the zygomatic arches 8 along the lower sides of the eye socket orbits 9. Thereby, incident light rays directed to the cheekbones or zygomatic arch skin areas is substantially absorbed and reflection into the eyes 10 is avoided.

Figure 2:
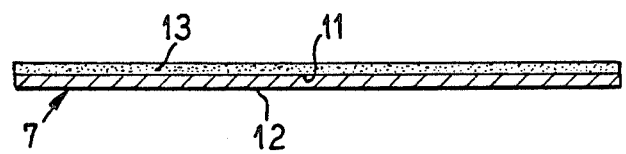
FIG. 2 is an enlarged sectional detail view taken substantially along the line II—II in FIG. 1.

In a desirable structure, the patches 7 are formed from an air pervious sheet material providing a body 11 (FIG. 2) which has on one face a light absorbing surface 12 and which is provided on the opposite face with a porous or at least air pervious pressure sensitive means comprising an adhesive layer 13.

For the body sheet layer 11, any economically feasible, self-sustaining, pliable sheet material may be used such as a medical grade air permeable tissue. This may be a felted fibrous material such as semi-bleached craft, porous thin plastic sheet, plastic mixed or impregnated paper tissue, or any other thin sheet material such as may be used for medical adhesive bandages, and which is susceptible to mass production die cutting or stamping of the patches 7.

As to the light absorbing coating 12, while it may be a coloring material or dye which permeates the body layer 11, the light absorbing surface 12 may comprise a non-reflective, such as black, hypo-allergenic coating uniformly applied over the surface of the body sheet 11.

A non-sensitizing pure acrylic copolymer porous adhesive which is non-irritating and incapable of sensitization on human skin is a preferred adhesive in the layer 13.

Figure 3:
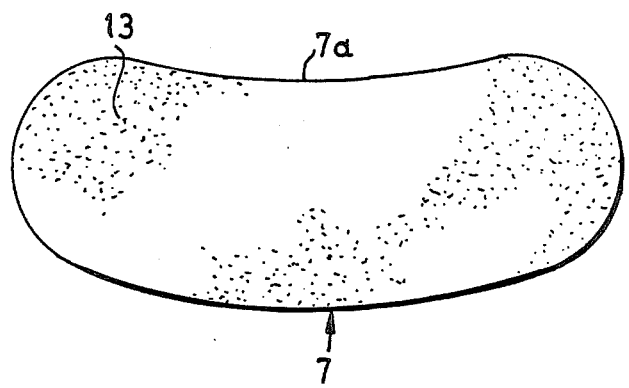
FIG. 3 is an enlarged plan view of a light absorbing patch embodying the present invention.

To meet average conditions, the size and shape of the patches 17 may be standardized at about 1½ inch (40 millimeter) in length by about ¾ inch (20 millimeters) in width. A generally kidney shape plan, that is a slightly parabolic outline is preferred for the patch 7 (FIG. 3). Thus the patch has a concavely arched edge 7a for disposition alignment to the eye socket formation along the orbit. Such shape and size will fit most zygomatic arch or cheekbone skin areas to receive the light absorbing patch 7.

Figure 4:
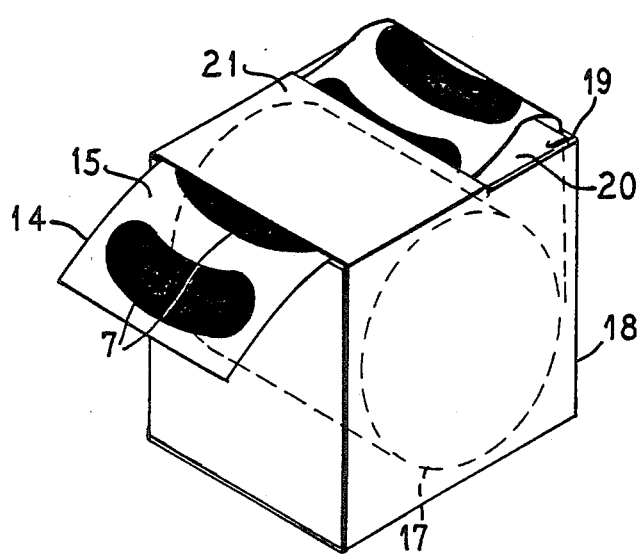
FIG. 4 is a perspective view of a dispenser for patches embodying the present invention.

For convenient handling and dispensing a quantity of the light absorbing patches 7, they may be carried seriatim on a carrier sheet in the form of a ribbon or strip 14 (FIG. 4) having a surface 15 treated to permit effective adhesive retention of the patches but from which the patches can be stripped for use. In a typical arrangement, the carrier strip 14 may comprise a roll 17 housed within a dispenser box 18 provided with a dispenser slot 19 in the rear of its top wall 20 and from which the strip 14 can be drawn forwardly under a guide bridge 21 overlying the front portion of the top wall 20. Through this arrangement, the carrier strip 14 can be easily transported with, for example, about five hundred of the patches 7 mounted thereon for serial removal for use as needed by stripping the same from the forwardly projecting end portion of the carrier ribbon. This dispenser package is quite convenient for transportation and handling of the patches so that they will be handy for instant use, such as in locker rooms and at playing fields, and convenient for team travel transportation.

In use, as each of the patches 7 is stripped from the carrier strip 14, the patch is applied to the user's zygomatic arch skin area with its concave edge 20 (FIGS. 1 and 3) generally adjacent to the orbit 9 of the eye 10 in association with which it is desired to at least greatly reduce reflection of incident light such as may be encountered on a playing field in sunny weather or under artificial illumination. Generally an individual one of the patches 7 is applied adjacent to each of the eyes 10.

Although a major utility for the patches 7 is in connection with athletic activity such as football, baseball, basketball, tennis, golf, and the like, the patches are useful for their light absorbing function in any circumstances where reflection into the eyes of incident light rays from the zygomatic arch skin surfaces is a problem, such as in the military and armed forces where light glare can interfere with performance.

There is no mess involved since the patches 7 are applied without need for any cream or greasy film. The face may be washed and dried, or dried of perspiration without disturbing the applied patches 7 or causing any smear.

When it is desired to remove the patch 7, they can be easily stripped because the pressure sensitive adhesive 13, although having held the respective patch thoroughly in use, permits ready stripping of the patch as desired. There will be no need to scrub the face to remove any greasy films. Since the patches 7 are relatively inexpensive, they may be freely discarded after peeling from the face.

Due to the air permeability of the patches 7, the skin underlying each patch may breath the patches permit oxygen penetration to the skin and moisture is substantially released. The problem of blocked pores from greasy films is avoided.

Because the patches 7 are thin and pliable they can be worn with utmost physical comfort. Eye comfort is enhanced by the substantial freedom from under the eye skin reflected eye glare.

It will be understood that variations and modifications may be effected without departing from the spirit and scope of the novel concepts of this invention.

We claim as our invention:

1. An under-eye light absorbing device, comprising:
   a replaceable pliable sheet material patch having a first face for generally comfortable application to the skin area on the zygomatic arch along the lower side of the orbit of a user, said patch being of sufficient extent to substantially cover the skin area on the zygomatic arch when applied to said skin area;
   pressure sensitive adhesive means on said first face for strippable adhesive retention of the patch on said skin area, said adhesive means removable holding said patch on said skin area, said adhesive means being resistant to perspiration to retain said patch on said skin area during exercise; and
   a light absorbing surface on a second face of the patch for absorbing incident light rays directed toward said skin area; said light absorbing surface being dark in color to reduce glare by substantially preventing light from reflecting from said skin area of the zygomatic arch toward the eyes of the wearer, said light absorbing surface being resistant to running caused by perspiration.

2. A device according to claim 1, wherein said patch comprises a medical grade tissue sheet material and said adhesive comprises an acrylic porous adhesive layer.

3. A device according to claim 1, wherein said light absorbing surface comprises a non-reflective non-smearing black hypoallergenic coating.

4. A device according to claim 1, wherein said patch comprises a body of semi-bleach porous craft paper.

5. A device according to claim 1, wherein said patch is generally kidney shaped in outline and of a length and width for generally conforming to the shape of the zygomatic arch skin area to which applied, with a concavely arched edge on the patch for disposition adjacent to the eye socket formation along the orbit.

6. A device according to claim 1, in combination with a series of identical devices carried on a dispensing ribbon strip, said dispensing strip being housed within a container, said container having means for facilitating seriatim dispensing of the patches by pulling the strip from the container, said ribbon having a surface to which the patches are attached releasably by means of the pressure sensitive adhesive and from which strip surface the patches can be readily stripped for use.

7. A device according to claim 1, wherein said light absorbing surface is black.

8. An under-eye light absorbing patch, comprising:
   a thin sheet body having a generally kidney-shaped outline in plan and being of about 1½ inch (40 millimeter) length and ¾ inch (20 millimeter) width for comfortable reception on the skin area of the zygomatic arch along the lower side of each obrbit of a user, said body being porous and being capable of substantially covering the skin area of the zygomatic arch when applied to said skin area;
   a layer of porous pressure sensitive adhesive on one face of said body by which the patch can be applied to said skin area and retained but from which area the patch can be readily stripped when desired, said adhesive being resistant to perspiration to retain said body on said skin area during exercise; and
   an opposite face on said body having a light absorbing surface which is exposed for capturing and preventing reflection into the associated eye of incident light rays striking said light absorbing surface, said light absorbing surface being dark in color to substantially prevent light rays from reflecting from said skin area of the zygomatic arch toward the eyes of the user so that glare is reduced and being resistant to running from perspiration to reduce the chance of foreign matter getting in the eyes of a user.

9. A patch according to claim 8, wherein said light absorbing surface is black.

10. A patch according to claim 8, including means for carrying the patch until it is used and comprising a patch carrier sheet having a release surface on which the pressure sensitive adhesive surface of the patch is attached and from which the patch can be stripped for use.

11. A method of absorbing incident light from the skin area on the zygomatic arch of a user along the lower side of the orbit, comprising:
   applying a black pliable porous patch to said skin area to substantially cover said skin area of the zygomatic arch and substantially reduce reflections of light from the area of the zygomatic arch toward the eyes; and adhesively attaching said patch to said skin area by a pressure sensitive adhesive to removably retain said patch over said skin area of the zygomatic arch and reduce the chance of inadvertent removal of said patch from said skin area.

12. A method according to claim 11, which comprises providing said patch of a generally kidney-shaped outline to facilitate reception of the patch on said skin area.

13. A method according to claim 11, which comprises providing said patch of a generally kidney-shaped outline to facilitate reception of the patch on said skin area.

14. A method according to claim 11, which comprises applying a respective one of said patches to each of the zygomatic arch skin areas of a user.

15. A method according to claim 11, which comprises dispensing said patch from a carrier strip, and in such dispensing stripping the patch from the carrier strip.

16. A method according to claim 15, which comprises dispensing said strip from a roll carried within a dispenser container.

* * * * *